(12) United States Patent
Nishide et al.

(10) Patent No.: US 9,149,604 B2
(45) Date of Patent: Oct. 6, 2015

(54) ASPIRATION CATHETER

(75) Inventors: Takuji Nishide, Settsu (JP); Masato Hashiba, Kanagawa (JP); Shogo Miki, Kanagawa (JP)

(73) Assignee: KANEKA CORPORATION, Osaka (JP)

( * ) Notice: Subject to any disclaimer, the term of this patent is extended or adjusted under 35 U.S.C. 154(b) by 1771 days.

(21) Appl. No.: 10/576,534

(22) PCT Filed: Oct. 26, 2004

(86) PCT No.: PCT/JP2004/016205
§ 371 (c)(1),
(2), (4) Date: Apr. 9, 2007

(87) PCT Pub. No.: WO2005/044359
PCT Pub. Date: May 19, 2005

(65) Prior Publication Data
US 2007/0191812 A1  Aug. 16, 2007

(30) Foreign Application Priority Data

Nov. 7, 2003 (JP) .................................. 2003-378329

(51) Int. Cl.
*A61M 5/178* (2006.01)
*A61M 25/00* (2006.01)
(Continued)

(52) U.S. Cl.
CPC ......... *A61M 25/0102* (2013.01); *A61M 25/003* (2013.01); *A61M 25/0043* (2013.01);
(Continued)

(58) Field of Classification Search
CPC ............. A61M 2025/0063; A61M 2025/0183; A61M 2025/1056; A61M 25/0023; A61M 25/003; A61M 25/0043; A61M 25/0102

USPC ............... 604/264, 272, 523, 528, 103.04, 604/164.13; 600/433–435, 585
See application file for complete search history.

(56) References Cited

U.S. PATENT DOCUMENTS 4,068,659 A    1/1978  Moorehead
5,047,018 A    9/1991  Gay et al. ...................... 604/164
(Continued)

FOREIGN PATENT DOCUMENTS

EP    0 242 985    10/1987
EP    0 728 496    8/1996
(Continued)

OTHER PUBLICATIONS

Erhard E. Starck, M.D., et al.; "Percutaneous Aspiration Thromboembolectomy"; Interventional Radiology; Jul. 1985; pp. 156:61-66.
(Continued)

*Primary Examiner* — Rebecca E Eisenberg
(74) *Attorney, Agent, or Firm* — Kratz, Quintos & Hanson, LLP

(57) ABSTRACT

There has been a demand for an aspiration catheter which has a sufficient amount of aspiration, which is sufficiently flexible to satisfactorily track tortuous blood vessels, in which the possibility of kinking of a catheter shaft is decreased when the aspiration catheter is inserted into a guiding catheter from outside of the body, and in which good operationality is achieved. An aspiration catheter of the present invention includes an aspiration lumen for removing a substance by aspiration, the aspiration lumen extending to a hub provided at the proximal end of the catheter; and a detachable core wire disposed in the aspiration lumen.

17 Claims, 10 Drawing Sheets

(51) Int. Cl.
*A61M 25/01* (2006.01)
*A61M 25/10* (2013.01)

(52) U.S. Cl.
CPC .... *A61M25/0023* (2013.01); *A61M 2025/0063* (2013.01); *A61M 2025/0183* (2013.01); *A61M 2025/1056* (2013.01)

(56) References Cited

U.S. PATENT DOCUMENTS

| | | | |
|---|---|---|---|
| 5,190,528 A | | 3/1993 | Fonger et al. ............... 604/171 |
| 5,378,234 A | * | 1/1995 | Hammerslag et al. ..... 604/95.04 |
| 5,421,826 A | * | 6/1995 | Crocker et al. .............. 604/509 |
| 5,667,521 A | * | 9/1997 | Keown ......................... 606/194 |
| 5,782,740 A | | 7/1998 | Schneiderman ................. 600/1 |
| 5,833,644 A | * | 11/1998 | Zadno-Azizi et al. ........ 604/509 |
| 6,152,909 A | | 11/2000 | Bagaoisan et al. |
| 6,159,195 A | * | 12/2000 | Ha et al. ....................... 604/500 |
| 6,663,613 B1 | * | 12/2003 | Evans et al. .................. 604/523 |
| 2001/0007922 A1 | * | 7/2001 | Schwager ..................... 600/485 |
| 2002/0177800 A1 | * | 11/2002 | Bagaoisan et al. ........... 604/6.12 |
| 2003/0195500 A1 | * | 10/2003 | Moorman et al. ............. 606/33 |
| 2004/0106866 A1 | * | 6/2004 | Ookubo et al. ............... 600/437 |
| 2004/0267280 A1 | | 12/2004 | Nishide et al. ................ 606/108 |
| 2005/0027236 A1 | * | 2/2005 | Douk ............................ 604/40 |
| 2005/0119615 A1 | * | 6/2005 | Noriega et al. ............ 604/95.04 |
| 2005/0240165 A1 | * | 10/2005 | Miki et al. .................... 604/528 |
| 2006/0041246 A1 | * | 2/2006 | Provost-tine et al. ........ 604/528 |
| 2007/0088323 A1 | * | 4/2007 | Campbell et al. ............. 604/523 |

FOREIGN PATENT DOCUMENTS

| | | |
|---|---|---|
| EP | 0 750 879 | 1/1997 |
| EP | 0 829 269 | 3/1998 |
| JP | 59-151969 | 8/1984 |
| JP | 62-243566 | 10/1987 |
| JP | 05-253304 | 10/1993 |
| JP | 6-3353 | 1/1994 |
| JP | 06-502327 | 3/1994 |
| JP | 07-024060 | 1/1995 |
| JP | 7-505559 | 6/1995 |
| JP | 9-10182 | 1/1997 |
| JP | 9-511159 | 11/1997 |
| JP | 10-085339 | 4/1998 |
| JP | 10-85339 | 4/1998 |
| JP | 10-127790 | 5/1998 |
| JP | 2001-029449 | 2/2001 |
| JP | 2002-102359 | 4/2002 |
| JP | 3318921 | 6/2002 |
| JP | 2002-291900 | 10/2002 |
| JP | 2003-102841 | 4/2003 |
| JP | 2003-284780 | 10/2003 |
| JP | 2004-130110 | 4/2004 |
| WO | WO 92/06733 | 4/1992 |
| WO | WO 94/18886 | 9/1994 |
| WO | WO 95/21652 | 8/1995 |

OTHER PUBLICATIONS

'87 General Brochure of silicone products for medical use with partial English translation; 6 pages.

* cited by examiner

ASPIRATION CATHETER

CROSS-REFERENCE TO THE RELATED APPLICATIONS

This application is a national phase of PCT application No. PCT/JP2004/016205 filed Oct. 26, 2004, the entire contents of which are incorporated by reference. This application also claims benefit of priority under 35 U.S.C. §119 to Japanese Patent Application No. 2003-378329 filed Nov. 7, 2003, the entire contents of which are incorporated by reference.

TECHNICAL FIELD

The present invention relates to a catheter percutaneously and transluminally introduced into the body to remove by aspiration a substance present in the body, and in particular, the invention relates to an aspiration catheter for removing by aspiration thrombi formed in the internal blood vessels and debris, such as atheromas, released in the blood vessels, by applying a negative pressure from the proximal end of the catheter.

BACKGROUND ART

Conventionally, when stenosis or occlusion occurs in vessels, such as blood vessels, and when blood vessels are blocked by thrombi, angioplasties (e.g., PTA: Percutaneous Transluminal Angioplasty and PTCA: Percutaneous Transluminal Coronary Angioplasty) are commonly performed in order to dilate narrowed areas or reopen occluded areas of blood vessels so that blood flow in the peripheries of blood vessels is improved. Many angioplasties have been performed in many medical institutions. Furthermore, in recent years, stents have been used to maintain the dilated state of narrowed areas in many cases.

A balloon catheter for PTA or PTCA is used together with a guiding catheter and a guidewire mainly for the purpose of dilating a narrowed area or occluded area of a blood vessel. In an angioplasty for the coronary artery using the balloon catheter, first, the guiding catheter is inserted into the femoral artery and advanced through the aorta, and the guiding catheter is positioned in the opening of the coronary artery. Then, the guidewire passing through the balloon catheter is advanced beyond the narrowed area or occluded area of the blood vessel. The balloon is inflated while being positioned at the narrowed area or occluded area so that the narrowed area or occluded area is dilated. The balloon is then deflated and removed from the body. The application of the balloon catheter is not limited to treatment of narrowed areas or occluded areas of blood vessels, and the balloon catheter is also useful for many other medical applications, such as insertion into blood vessels and insertion into various body cavities and tubular tissue structures.

However, when occlusion is caused by thrombi in the blood vessel, if the occluded area is dilated by the balloon catheter, there may be a possibility that the thrombi are detached from the inner wall of the blood vessel to occlude peripheral vessels downstream. In the case of the narrowed area of the blood vessel in which the lesion contains many athero-plaques, there may be a possibility that dilation by the balloon catheter leads to scattering of the athero-plaques (atheromas) to occlude peripheral vessels. When peripheral vessels are blocked as described above, even if the occluded area or narrowed area is dilated, blood is prevented from flowing into the peripheries, resulting in slow-flow or no-reflow.

When such a situation arises, in the coronary artery or the like, it is general practice to wait and see if the blood flow is recovered, but a long recovery time is required. According to circumstances, a vasodilator, such as nitroglycerin, may be administered to recover the blood flow, or a thrombolytic agent, such as urokinase, may be locally administered to dissolve the obstruction. In either case, a long recovery time is still required. When peripheral vessels are heavily occluded to produce poor hemodynamics, an auxiliary procedure, such as intra-aortic balloon pumping (IABP), may be used.

Besides the thrombolytic therapy, a method has been attempted in which thrombi are mechanically fragmented and a negative pressure is simultaneously applied from the proximal end of the catheter to remove the thrombi from the body. However, in order to fragment a thrombus at the catheter tip, it is of course necessary to efficiently transmit the mechanical power applied from the proximal end of the catheter to the distal end of the catheter. Consequently, in order to enhance the transmission of power in the catheter shaft, the entire catheter shaft must be composed of a relatively hard material, often resulting in difficulty in advancing the catheter to the target site in the blood vessel. Furthermore, since a negative pressure must be applied from the proximal end of the catheter simultaneously with the application of mechanical power, a large-scale device is required, and thus this method has not become widely used.

On the other hand, the effect of a catheter having a simple structure in which thrombi are removed by aspiration from the body by the application of a negative pressure from the proximal end has been being clinically confirmed. However, the cross-sectional area of the aspiration lumen for aspiration is not sufficiently secured, and only catheters having low aspiration capability are available. The reason for this is that the catheter is advanced over the guidewire to the target site in the blood vessel. Namely, since a guidewire lumen tracking the guidewire is provided in the aspiration lumen, it is not possible to secure a sufficient aspiration lumen.

On the other hand, in a structure in which a guidewire lumen is provided outside an aspiration lumen, the outer diameter of the aspiration catheter inevitably increases. Consequently, the outer diameter of the guiding catheter used together increases so that a sufficient inner diameter is secured, resulting in an enormous burden to the patient.

In addition, since any of the guidewire lumens described above usually has a length of about 30 cm from the tip of the aspiration catheter, the entire catheter shaft lacks flexibility, resulting in poor insertability into tortuous blood vessels.

Patent Document 1 discloses a catheter that is insertable into a blood vessel without a guidewire. The catheter includes a passage for injecting a drug solution, an imaging agent, or the like, disposed therein; a hub disposed at the proximal end thereof; and a superelastic wire provided with a detachable hub. In order to increase the rate of injection of a drug solution, an imaging agent, or the like, from the hub, the superelastic wire is designed to be withdrawn from the catheter so that the effective lumen of the internal injection passage is increased. However, when a catheter having such a structure is used as an aspiration catheter in a conventional PTCA procedure, it is not possible to advance the catheter to an affected site over a guidewire, and low operationality has been pointed out as a problem.

[Patent Document 1] Japanese Examined Patent Application Publication No. 3-74590

DISCLOSURE OF INVENTION

In order to overcome the problems described above, it is an object of the present invention to provide an aspiration catheter which secures a largest possible aspiration lumen, which is sufficiently flexible to be advanced to a target site following a guidewire and to satisfactorily track tortuous blood vessels, and in which the possibility of kinking of the catheter shaft is decreased when the aspiration catheter is inserted into a guiding catheter from outside the body, thus achieving good operationality.

As a result of intensive research conducted by the present inventors, it has been found that the problems can be overcome by an aspiration catheter having the following structure, and thus the present invention has been completed.

Namely, an aspiration catheter for removing by aspiration a substance from a living body includes a main shaft including a distal shaft and a proximal shaft, the main shaft having an aspiration lumen disposed therein, the aspiration lumen being used for removing the substance by aspiration; a guidewire shaft disposed at the distal region of the distal shaft, the guidewire shaft having a guidewire lumen into which a guidewire is insertable, the guidewire lumen being disposed in the guidewire; a hub provided at the proximal end of the proximal shaft, the aspiration lumen extending to the hub; and a detachable core wire disposed in the aspiration lumen.

The present invention also relates to the aspiration catheter, in which a connector is fixed on the proximal end of the core wire, and the connector is mounted to the proximal end of the hub in a detachable manner.

The present invention also relates to the aspiration catheter, in which the interior of the aspiration lumen can be flushed through the connector with the connector being mounted in a detachable manner.

The present invention also relates to the aspiration catheter, in which the distal end of the core wire recedes from the distal end of the aspiration lumen in the proximal direction.

The present invention also relates to the aspiration catheter, in which the relationship $0.3 \leq R1/R2 \leq 0.9$ is satisfied, and more preferably, the relationship $0.4 \leq R1/R2 \leq 0.7$ is satisfied, wherein R1 is the maximum outer diameter of the core wire, and R2 is the minimum inner diameter of the aspiration lumen located on the distal side of the hub.

The present invention also relates to the aspiration catheter, in which the core wire is a spring wire made of coiled metal wire.

The present invention also relates to the aspiration catheter, in which at least a portion of the core wire has a tapered shape in which the outer diameter becomes larger toward the proximal end.

The present invention also relates to the aspiration catheter, in which at least a portion of the core wire has flexibility which becomes higher toward the distal end.

The present invention also relates to the aspiration catheter, in which the core wire is composed of stainless steel, a Co—Cr alloy, an Ni—Ti alloy, an Ni—Ti—Fe alloy, an Ni—Ti—Cu alloy, an Ni—Ti—Cr alloy, an Ni—Ti—V alloy, an Ni—Ti—Co alloy, an Ni—Ti—Nb alloy, an Ni—Ti—Pd alloy, an Ni—Ti—Cu—Cr alloy, or a composite thereof.

The present invention also relates to the aspiration catheter, in which the tip of the distal shaft is obliquely cut, the distal end of the guidewire shaft is positioned at the obliquely cut distal end of the distal shaft or protrudes from the distal end of the distal shaft in the distal direction, and the relationship $0.5 \leq L2/L1$ is satisfied, wherein L1 is the length of the obliquely cut portion of the distal shaft in the longitudinal direction of the catheter, and L2 is the length from the proximal end of the guidewire shaft to the distal end of the distal shaft.

The present invention also relates to the aspiration catheter, in which the relationship $2 \text{ mm} \leq L1 \leq 10 \text{ mm}$ is satisfied.

The present invention also relates to the aspiration catheter, in which the guidewire shaft is provided with a radiopaque marker.

The present invention also relates to the aspiration catheter, in which the proximal shaft is composed of a polyimide.

The present invention also relates to the aspiration catheter, in which the proximal shaft is composed of a braided tube in which a metal braid and a polymer material are combined.

The present invention also relates to the aspiration catheter, in which the braided tube includes an inner layer defining the aspiration lumen, a metal braid disposed on the outer surface of the inner layer, and an outer layer disposed on the outer surface of the metal braid.

The present invention also relates to the aspiration catheter, in which at least a proximal portion of the proximal shaft has a flexural modulus of 1 GPa or more.

The present invention also relates to the aspiration catheter, in which at least a portion of the distal shaft is applied with a hydrophilic coating that exhibits a lubricating property in a wet environment.

Furthermore, the present invention relates to a method for using the aspiration catheter including the steps of inserting the aspiration catheter into a living body with the core wire being present in the aspiration lumen, then withdrawing the core wire, and applying a negative pressure to the aspiration lumen to remove by aspiration a substance from the living body.

Figure 1:
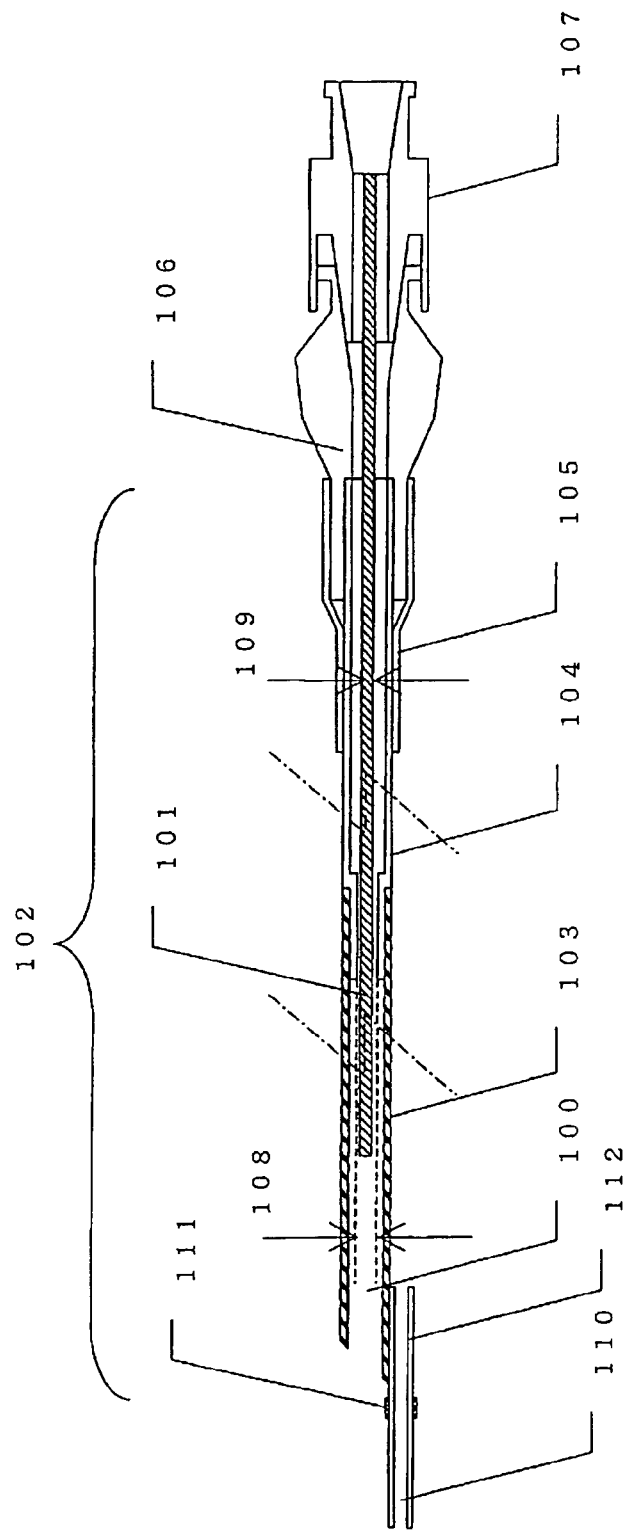
FIG. 1 is a cross-sectional view showing an aspiration catheter in an embodiment of the present invention.

In the drawings, reference numeral 100 represents an aspiration lumen, 101 a core wire, 102 a main shaft, 103 a distal shaft, 104 a proximal shaft, 105 a strain relief, 106 a hub, 107 a connector, 108 a minimum inner diameter of the aspiration lumen, 109 a maximum outer diameter of the core wire, 110 a guidewire lumen, 111 a radiopaque marker, and 112 a guidewire shaft.

Furthermore, in the drawings, reference numeral 113 represents a tank, 114 a plate including a bent portion, 115 a simulated aorta, 116 a guiding catheter, and 117 a hemostasis valve. Furthermore, reference numeral 118 represents a polyethylene tube, 119 a bent portion, 120 a linear portion, 121 an outer diameter of the polyethylene tube, 122 an inner diameter of the polyethylene tube, and 123 a guidewire.

BEST MODE FOR CARRYING OUT THE INVENTION

The embodiments of the aspiration catheter of the present invention will be described in detail with reference to the drawings. However, it is to be understood that the present invention is not limited thereto.

Figure 2:
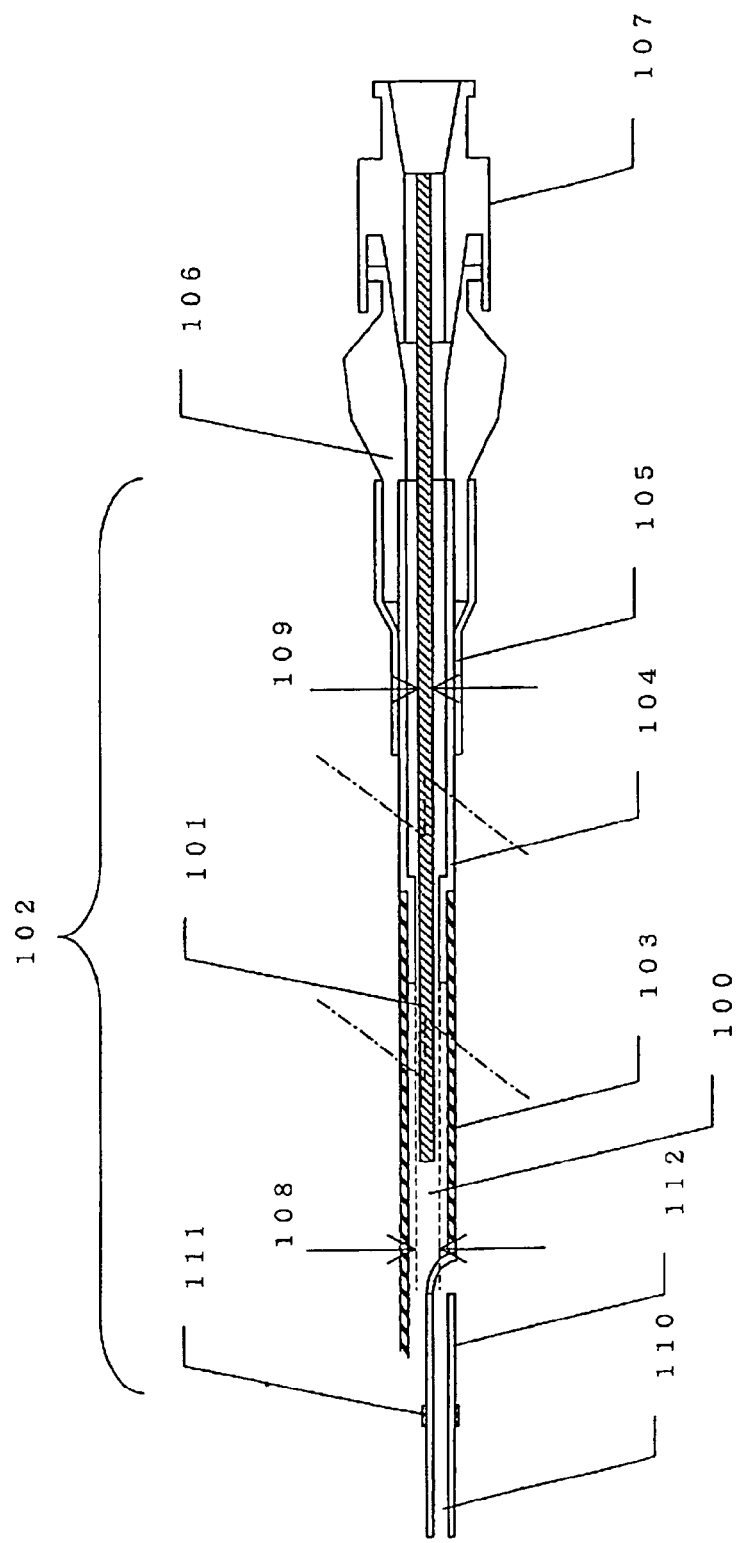
FIG. 2 is a cross-sectional view showing an aspiration catheter in another embodiment of the present invention.

As shown in the embodiment of FIG. 1 or 2, an aspiration catheter of the present invention includes a main shaft 102 including a distal shaft 103 and a proximal shaft 104, the main shaft 102 having an aspiration lumen 100 disposed therein, the aspiration lumen 100 being used for removing a substance by aspiration; a guidewire shaft 112 disposed at the distal region of the distal shaft 103, the guidewire shaft 112 having a guidewire lumen 110 into which a guidewire is insertable, the guidewire lumen 110 being disposed in the guidewire shaft 112; a hub 106 provided at the proximal end of the proximal shaft 104, the aspiration lumen 100 extending to the hub 106; and a detachable core wire 101 disposed in the aspiration lumen 100. By providing the core wire 101 in the aspiration lumen 100, the possibility of kinking of the catheter shaft is effectively decreased when the aspiration catheter is inserted into a guiding catheter from outside the body, thus achieving good operationality. Furthermore, since the guidewire lumen 110 is provided, the aspiration catheter can be easily advanced to tortuous sites over a guidewire.

Figure 3:
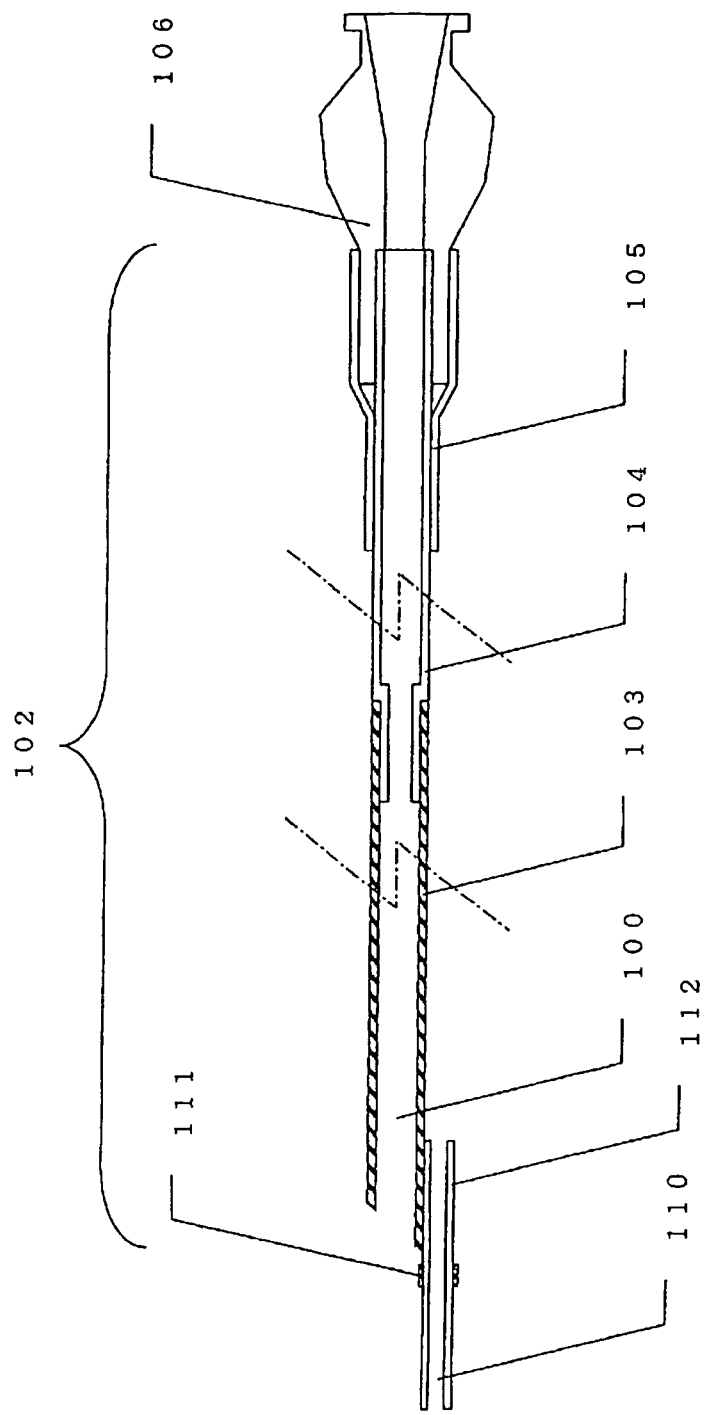
FIG. 3 is a cross-sectional view showing the aspiration catheter shown in FIG. 1 from which a core wire is withdrawn.
Figure 4:
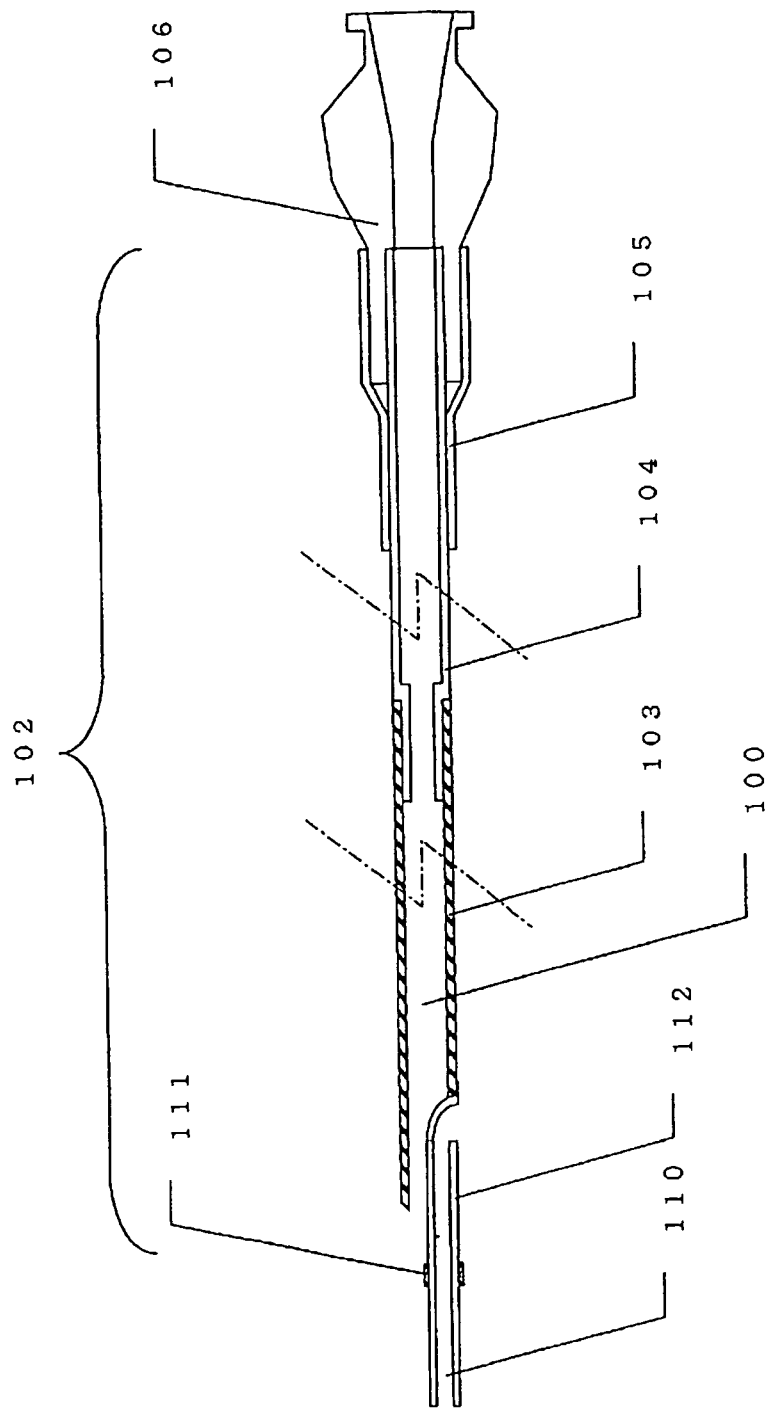
FIG. 4 is a cross-sectional view showing the aspiration catheter shown in FIG. 2 from which a core wire is withdrawn.

If the core wire 101 is provided in the aspiration lumen 100, the cross-sectional area of the aspiration lumen 100 decreases, and thus it is not possible to achieve a sufficient amount of aspiration. However, in the present invention, since the core wire 101 is provided in a detachable manner, it is possible to remove the core wire 101 during aspiration as shown in the embodiment of FIG. 3 or 4. Therefore, a sufficient amount of aspiration can be easily achieved. In an aspiration catheter in which the core wire 101 is fixed, an increase in the cross-sectional area of the aspiration lumen 100 is the only way to achieve the same amount of aspiration as in the aspiration catheter of the present invention, resulting in an increase in the outer diameter of the catheter shaft. If the outer diameter of the catheter shaft is increased, the size of a guiding catheter or a sheath used for insertion of the aspiration catheter must be increased, thus increasing the burden on a patient undergoing aspiration treatment, which is undesirable.

The aspiration catheter of the present invention is characterized by the inclusion of the detachable core wire 101 as described above. The mechanism for allowing the core wire 101 to be detachable is not particularly limited. However, in consideration of operationality during the detachment of the core wire 101, preferably, a connector 107 is fixed on the proximal end of the core wire 101, and the connector 107 is mounted to the proximal end of the hub 106 in a detachable manner. The method for fixing between the proximal end of the core wire 101 and the connector 107 does not restrict the advantageous effects of the present invention at all, and fixing may be performed using an adhesive or the like. In such a case, the type of adhesive used is not particularly limited. The method for connecting the connector 107 to the proximal end of the hub 106 is not limited as long as the connector 107 is detachable. In one preferred embodiment, the distal end of the hub 106 is formed as a female Luer adaptor and the connector 107 is formed as a male Luer adaptor. Thereby, the core wire 101 can be reliably and easily detached. Furthermore, by forming the proximal end of the hub 106 as a female Luer adaptor, it is also possible to simply apply a negative pressure to the aspiration lumen 100 using a syringe or the like.

As described above, when the connector 107 is fixed on the proximal end of the core wire 101 and the connector 107 is mounted to the proximal end of the hub 106 in a detachable manner, it is possible to achieve a structure in which the aspiration lumen 100 is flushed through the connector 107. When the aspiration catheter of the present invention is used, it is necessary to flush the aspiration lumen 100 with a suitable solution, such as a solution of physiological heparinized saline, before insertion into the body. Flushing prevents thrombus formation when the aspiration catheter is inserted into the body, in particular, the blood vessels. Flushing is usually performed using a syringe. Consequently, by forming the proximal end of the connector 107 as a female Luer adaptor, it is possible to perform flushing with the core wire 101 being mounted, and it is possible to insert the aspiration catheter into the body promptly after flushing to start treatment.

The positional relationship between the guidewire lumen 110 and the aspiration lumen 100 does not restrict the advantageous effects of the present invention at all. As shown in FIG. 1, the guidewire lumen 110 and the aspiration lumen 100 may be disposed independently of each other. As shown in FIG. 2, the guidewire lumen 110 may be partially disposed inside the aspiration lumen 100. Alternatively, the guidewire lumen 110 may be entirely disposed inside the aspiration lumen 100. However, when the guidewire lumen 110 is partially or entirely disposed inside the aspiration lumen 100, the cross-sectional area of the aspiration lumen 100 is smaller compared with the case in which the guidewire lumen 110 and the aspiration lumen 100 are disposed independently of each other. In particular, an increase in the length in the longitudinal direction of the portion of the guidewire lumen 110 disposed inside the aspiration lumen 100 leads to a decrease in the amount of aspiration. Therefore, the length of the portion of the guidewire lumen 110 disposed inside the aspiration lumen 100 is preferably as small as possible. On the other hand, when the guidewire lumen 110 and the aspiration lumen 100 are disposed independently of each other, there is an increased risk that the guidewire shaft 112 will be separated from the distal shaft 103 when the aspiration catheter is inserted or withdrawn along a guidewire. It is also possible to reinforce the joint between the guidewire shaft 112 and the distal shaft 103 using another component. In such a case, however, the outer diameter of the joint significantly increases. As described above, the aspiration ability and safety of the catheter greatly depend on the positional relationship between the guidewire lumen 110 and the aspiration lumen 100. Therefore, it is obvious to those skilled in the art that the aspiration catheter can be appropriately designed in consideration of the target site to be treated, method for use, required amount of aspiration, substance subjected to aspiration, etc.

With respect to the material for the guidewire shaft 112, in order to secure good slidability with a guidewire, at least the inner surface thereof is preferably composed of a polyolefin, in particular, a polyethylene.

The method for bonding between the distal shaft 103 and the guidewire shaft 112 does not restrict the advantageous effects of the present invention at all. Namely, if the distal shaft 103 and the guidewire shaft 112 are composed of materials that can be welded to each other, bonding can be performed by welding. Alternatively, if the distal shaft 103 and the guidewire shaft 112 are composed of materials that cannot exhibit sufficient bonding strength when welded, bonding may be performed using an adhesive. In such a case, the chemical species in the adhesive used is not particularly limited. For example, a cyanoacrylate, urethane, epoxy, or silicone adhesive is preferably used. The curing mechanism of the adhesive is also not particularly limited. For example, a moisture-curing, two-part curing, or photo-curable adhesive is suitably used. If the distal shaft 103 and the guidewire shaft 112 are composed of materials having poor adhesion properties, surface treatment may be performed, for example, by oxygen plasma or corona discharge, or using a silane coupling agent, before bonding.

Preferably, the distal end of the core wire 101 recedes from the distal end of the aspiration lumen 100 in the proximal direction. If the distal end of the core wire 101 protrudes from the distal end of the aspiration lumen 100, there is a high risk of internal injuries during insertion. Furthermore, after aspiration treatment is performed with the core wire 101 being dismounted, when it becomes necessary to move the aspiration catheter to treat another site and the core wire 101 is mounted inside the aspiration lumen 100, internal injuries due to the core wire 101 are highly likely to occur.

As long as the distal end of the core wire 101 recedes from the distal end of the aspiration lumen 100 in the proximal direction, the advantageous effects of the present invention are not restricted at all. The position of the distal end of the core wire 101 can be determined in consideration of kinking of the catheter shaft during insertion, operationality when the aspiration catheter is inserted or moved over a guidewire, rigidity balance of the entire aspiration catheter, etc.

Preferably, the relationship $0.3 \leq R1/R2 \leq 0.9$ is satisfied, wherein R1 is a maximum outer diameter 109 of the core wire 101, and R2 is a minimum inner diameter 108 of the aspiration lumen 100. If $R1/R2<0.3$, the core wire 101 is too thin relative to the aspiration lumen 100, and therefore the effect of preventing folding by the core wire 101 during insertion is not shown sufficiently. If $R1/R2>0.9$, the entire aspiration catheter becomes rigid, and it becomes extremely difficult to pass the aspiration catheter through the tortuous site. More preferably, the relationship $0.4 \leq R1/R2 \leq 0.7$ is satisfied.

Figure 5:
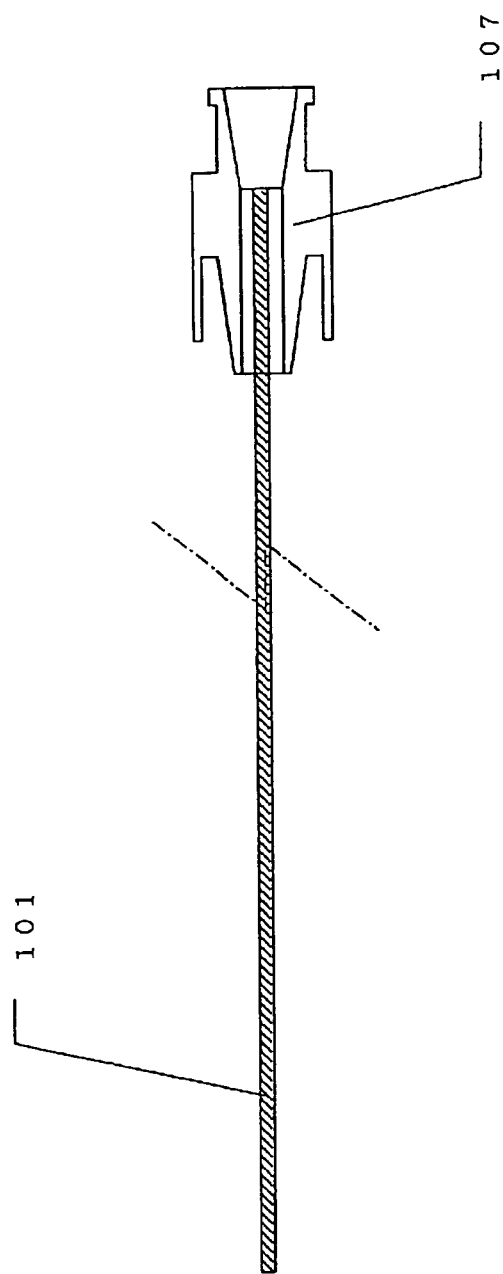
FIG. 5 is a cross-sectional view showing an example of core wire used in the aspiration catheter of the present invention.
Figure 6:
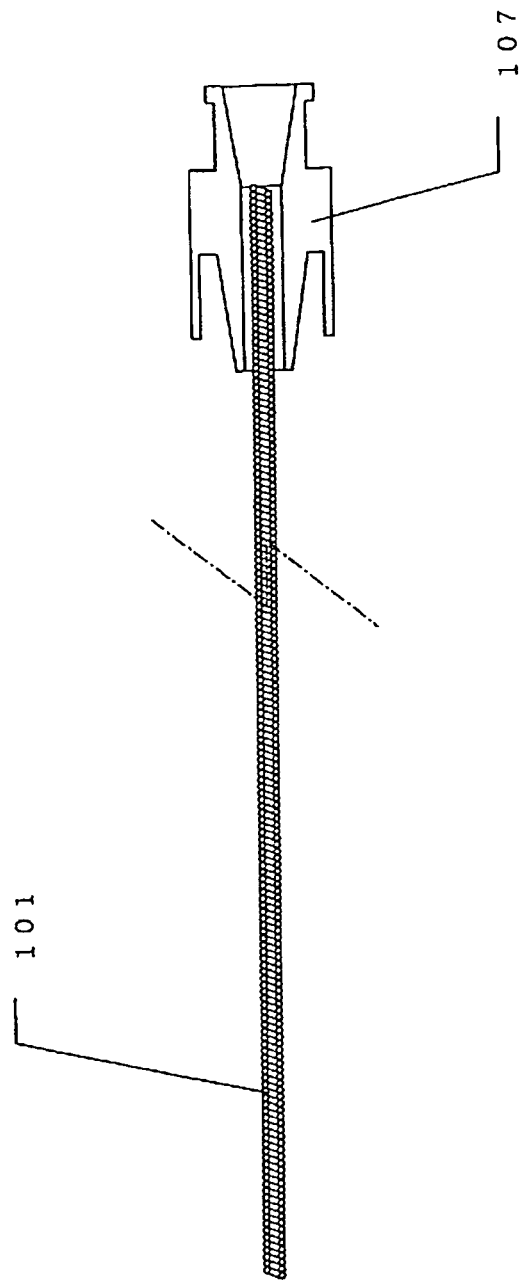
FIG. 6 is a cross-sectional view showing the other example of core wire used in the aspiration catheter of the present invention.

The structure and shape of the core wire 101 do not restrict the advantageous effects of the present invention at all. A typical example of the core wire 101 is one with a straight shape as shown in FIG. 5. From the standpoint of further improving the passability through tortuous sites, as shown in FIG. 6, preferably, the core wire 101 is a spring wire made of coiled metal wire. In such a case, the outer diameter, pitch, etc., of the wire constituting the spring wire are not particularly limited. The pitch of the spring wire may be changed continuously or stepwise so that the flexibility of the core wire 101 becomes higher toward the distal end. Furthermore, although not shown in FIG. 6, a core wire may be disposed inside the spring.

Figure 7:
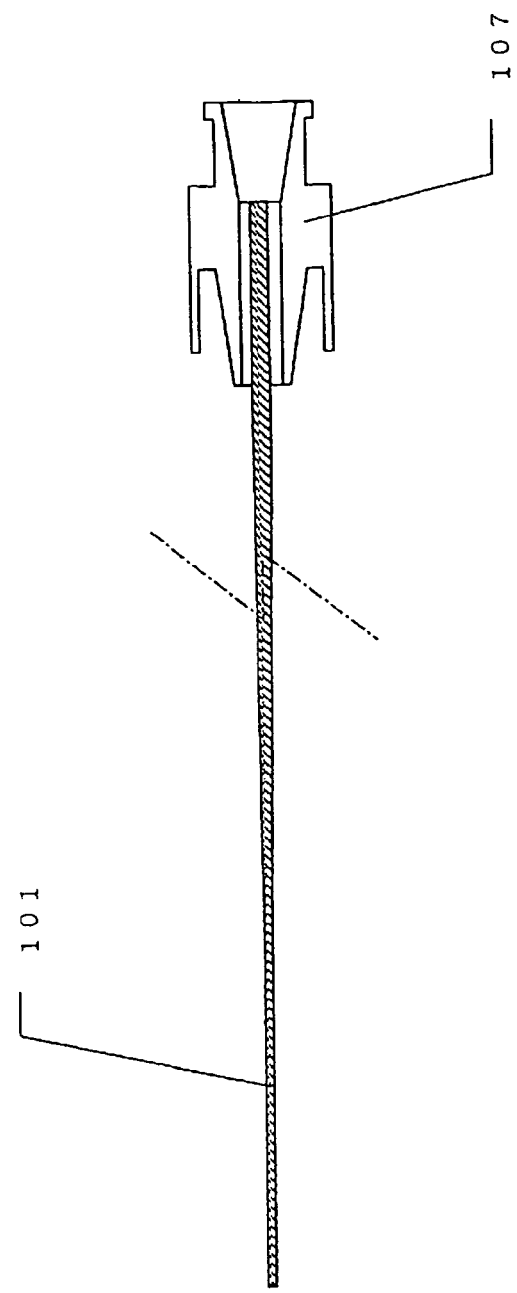
FIG. 7 is a cross-sectional view showing the other example of core wire used in the aspiration catheter of the present invention.

Although the straight shape is shown in FIG. 5 as the typical example, a tapered core wire 101 as shown in FIG. 7 may also be used suitably. When such a tapered wire is used, by controlling the tapered shape, it is possible to control the flexibility of the aspiration catheter.

In the core wire 101, preferably, the flexibility becomes higher toward the distal end. By increasing the flexibility of the core wire 101, passability can be enhanced in the case, for example, in which the site to be treated is tortuous, or the aspiration catheter must pass through a tortuous site to reach the site to be treated. Examples of the means for imparting flexibility include use of a spring wire or a tapered wire as the core wire 101 as described above. Further examples include a combination of a spring wire and a tapered shape, and provision of various cuts to the surface of a wire.

The core wire 101 is preferably composed of a metal in consideration of prevention of kinking of the aspiration catheter. In view of corrosion resistance, antithrombogenicity, etc., the core wire 101 is preferably composed of stainless steel or a Co—Cr alloy. Furthermore, a superelastic alloy may be used to prevent kinking of the core wire 101 itself. Examples of the superelastic alloy suitable for use include Ni—Ti alloys, Ni—Ti—Fe alloys, Ni—Ti—Cu alloys, Ni—Ti—Cr alloys, Ni—Ti—V alloys, Ni—Ti—Co alloys, Ni—Ti—Nb alloys, Ni—Ti—Pd alloys, and Ni—Ti—Cu—Cr alloys.

Preferably, the tip of the distal shaft 103 is obliquely cut. By cutting obliquely, a wide entrance of the aspiration lumen 100 can be secured, and thereby the aspiration efficiency can be increased. Preferably, the relationship $0.5 \leq L2/L1$ is satisfied, wherein L1 is the length of the obliquely cut portion of the distal shaft in the longitudinal direction of the catheter, and L2 is the length from the proximal end of the guidewire shaft 112 to the distal end of the distal shaft 103. If $L2/L1<0.5$, the area of the joint between the guidewire shaft 112 and the distal shaft 103 decreases, and the guidewire shaft 112 is highly likely to be separated from the distal shaft 103.

Preferably, the relationship $2 \text{ mm} \leq L1 \leq 10 \text{ mm}$ is satisfied. If L1 is less than 2 mm, it is difficult to remove debris by aspiration efficiently. If L1 exceeds 10 mm, there is an increased risk that the inner wall of the blood vessel will be damaged by the obliquely cut portion during the advancement of the aspiration catheter through the body, in particular, the tortuous blood vessel. In order to prevent internal injuries during insertion into the body or during aspiration treatment, the obliquely cut portion may be subjected to chamfering so that the edges are smoothened. Examples of the chamfering method which may be used include, but are not limited to, a method in which edges are melted by heating, and a mechanical polishing method.

In the aspiration catheter of the present invention, preferably, the guidewire shaft 112 is provided with a radiopaque marker 111. In such a case, more preferably, the radiopaque marker 111 is disposed at a position from which the position of the distal end of the aspiration lumen 100 can be confirmed. The radiopaque marker 111 makes it possible to confirm the position of the distal end of the aspiration lumen 100 during insertion of the aspiration catheter or during aspiration treatment, and therefore, the risk of internal injuries due to the obliquely cut tip of the distal shaft 103 is decreased.

The radiopaque marker 111 may be composed of any material that has sufficient radiopacity. Preferably, the radiopaque marker 111 is composed of a metal material, and examples thereof include gold, silver, platinum, tantalum, iridium, tungsten, and alloys of these metals. Furthermore, the structure of the radiopaque marker 111 does not restrict the advantageous effects of the present invention at all. The radiopaque marker 111 may be ring-shaped or braid-shaped, or may have a structure other than this. The method for fixing the radiopaque marker 111 is not particularly limited.

The proximal shaft 104 is preferably composed of a polyimide or a braided tube in which a metal wire and a polymer material are combined. With respect to the polyimide, because of its excellent tensile strength, tensile yield strength, and compressive strength, the thickness of the shaft can be decreased. With respect to the braided tube, by selecting the shape of the wire, number of wires, pitch, or type of polymer material used, the thickness of the shaft can be decreased as in the polyimide. By decreasing the thickness of the shaft, the diameter of the aspiration lumen 100 can be increased, resulting in significant improvement in the aspiration ability.

Preferably, the braided tube includes an inner layer defining the aspiration lumen 100, a metal braid disposed on the outer surface of the inner layer, and an outer layer disposed on the outer surface of the metal braid. Such a double layer structure allows the physical properties of the braided tube to be more finely controlled. For example, by using, as the inner layer, a fluorocarbon resin, such as polytetrafluoroethylene (PTFE), a tetrafluoroethylene•perfluoroalkylvinylether copolymer (PFA), a tetrafluoroethylene•hexafluoropropylene copolymer (FEP), a tetrafluoroethylene•ethylene copolymer (ETFE), poly(vinylidene fluoride) (PVDF), or polychlorotrifluoroethylene (PCTFE); high-density polyethylene; or the like, thrombi and atheromas are prevented from adhering to the interior of the aspiration lumen 100, and aspiration can be performed efficiently. By using, as the outer layer, an elastomer, such as a polyamide elastomer, a polyester elastomer, or a polyolefin elastomer, the strength and flexibility of the braided tube can be controlled.

The material and structure of the metal braid constituting the braided tube do not restrict the advantageous effects of the present invention at all, and various materials and structures may be used. Namely, a metal braid may be formed using one or a plurality of metal wires per group, each metal wire being obtained by processing stainless steel, e.g., SUS304 or SUS316, spring steel, piano wire, oil tempered wire, a Co—Cr alloy, an Ni—Ti alloy, or the like, so as to have a cross-section that is circular, oval, square, or the like. The number of metal wires per braid is not particularly limited.

Preferably, at least a proximal portion of the proximal shaft 104 is composed of high-modulus material with a flexural modulus of 1 GPa or more. By using the shaft composed of such a high-modulus material, power applied by the operator in operating the aspiration catheter can be fully transmitted to the tip of the catheter. Namely, in addition to the pushing force and the pulling force, the rotating force can be easily transmitted to the tip. Examples of the high-modulus material which may be suitably used include metal materials, such as stainless steel, Co—Cr alloys, and Ni—Ti alloys; and resin materials, such as polyimides, polyether ether ketones, and polyamide-imides. Composites of these materials may be used.

The distal shaft 103 is preferably composed of a material having a lower modulus compared with the proximal shaft 104 so that rigidity continuously changes in the longitudinal direction of the aspiration catheter. Examples of the material which may be suitably used for the distal shaft 103 include polyolefins (e.g. polyethylene), polyamides, polyesters, polyurethanes, polyolefin elastomers, polyamide elastomers, polyester elastomers, and polyurethane elastomers. The method for bonding the distal shaft 103 to the proximal shaft 104 is not particularly limited, and a known method, such as welding or adhesion, may be used.

The materials for a strain relief 105, which is used to reduce the difference in rigidity between the proximal shaft 104 and the hub 106, and the hub 106 do not restrict the advantageous effects of the present invention at all. In view of moldability, resin materials are preferably used for the strain relief 105 and the hub 106.

Preferably, at least a portion of the distal shaft 103 is applied with a hydrophilic coating that exhibits a lubricating property in a wet environment. In particular, in an aspiration catheter provided with the guidewire shaft 112, if the size of the aspiration lumen 100 is increased as much as possible, the outer diameter of the distal shaft 103 is increased. Consequently, when the aspiration catheter is inserted into a blood vessel in particular, there may be a possibility that the sliding friction of the aspiration catheter with the inner wall of the blood vessel increases because of the distal shaft 103. Therefore, at least a portion of the distal shaft 103 is preferably applied with a hydrophilic coating to reduce sliding friction. Of course, the distal shaft 103 may be entirely applied with a hydrophilic coating, or the proximal shaft 104 may be partially or entirely applied with a hydrophilic coating.

The advantageous effects of the present invention are not particularly restricted by the method for applying the hydrophilic coating and the material for the hydrophilic coating, and the method and the material may be appropriately selected depending on the materials of the distal shaft 103, the proximal shaft 104, the guidewire shaft 112, etc. For example, a hydrophilic polymer, such as poly(2-hydroxyethyl methacrylate), polyacrylamide, or polyvinylpyrrolidone, may be used. Furthermore, by adjusting the thickness of and the material for the hydrophilic coating in the longitudinal direction of each shaft, the sliding friction may be controlled so as to gradually increase or decrease.

A method for using the aspiration catheter according to the present invention includes the steps of inserting the aspiration catheter into a living body with the core wire 101 being present in the aspiration lumen 100, then withdrawing the core wire 101, and applying a negative pressure to the aspiration lumen 100 to remove by aspiration a substance from the living body. In this method, the method for applying a negative pressure to the aspiration lumen 100 is not particularly limited. For example, a negative pressure may be applied manually using a syringe equipped with a lock, or automatically using a pump or the like.

EXAMPLES

Examples and comparative examples of the present invention will be described in detail below.

Example 1

As a proximal shaft, a polyimide tube with an outer diameter of 1.30 mm, an inner diameter of 1.10 mm, and a length of 1,100 mm was formed by dip forming using a polyamic acid varnish. As a distal shaft, a tube with an outer diameter of 1.30 mm, an inner diameter of 1.00 mm, and a length of 300 mm was formed by extrusion molding of low-density polyethylene (LF480M, Japan Polychem Corporation). The diameter of one end of the proximal shaft was reduced by thermal drawing. The portion in which the diameter was reduced was inserted into the distal shaft and fixed by bonding using a two-part curing urethane adhesive (Nipporan 4235/Coronate 4403, Nippon Polyurethane Industry Co., Ltd.), and a main shaft was thereby obtained. Since the distal shaft was composed of a material with poor adhesion properties, oxygen plasma treatment was performed before bonding.

The tip of the distal shaft was obliquely cut so that the length L1 in the longitudinal direction of the catheter was 2 mm. A hub produced by injection molding of polycarbonate (Makrolon 2658, Bayer AG) and a strain relief produced by injection molding of a polyamide elastomer (PEBAX5533SA01, Elf Atochem, Inc.) were fixed on the proximal end of the proximal shaft by bonding using a two-part curing urethane adhesive (Nipporan 4235/Coronate 4403, Nippon Polyurethane Industry Co., Ltd.).

A tube with an outer diameter of 0.60 mm, an inner diameter of 0.42 mm, and a length of 10 mm was formed by extrusion molding of a high-density polyethylene (HY540, Japan Polychem Corporation), and a radiopaque marker composed of a platinum-tungsten alloy (tungsten content 8 wt %) with an outer diameter of 0.72 mm, an inner diameter of 0.65 mm, and a length of 1 mm was fixed by swaging on the center of the tube. A guidewire shaft was thereby produced. The guidewire shaft and the distal shaft were placed so that the length L2 was 1 mm and the guidewire shaft protrudes from the distal shaft in the distal direction, and bonded to each other by heat welding. During bonding, in order to secure a guidewire lumen and an aspiration lumen, mandrels were inserted into both shafts.

A straight wire composed of SUS304 alloy steel with an outer diameter of 0.605 mm and a length of 1,300 mm was used as a core wire. A connector produced by injection molding polycarbonate (Makrolon 2658, Bayer AG) was bonded to one end of the core wire using a two-part curing urethane adhesive (Nipporan 4235/Coronate 4403, Nippon Polyurethane Industry Co., Ltd.). The core wire was inserted, from the end not provided with the connector, through the hub, and the hub and the connector were fastened to each other. An aspiration catheter was thereby produced.

Example 2

An aspiration catheter was produced as in Example 1 except that a straight wire composed of SUS304 alloy steel with an outer diameter of 0.715 mm was used as a core wire.

Example 3

An aspiration catheter was produced as in Example 1 except that the guidewire shaft was placed inside the distal shaft and that a straight wire composed of an Ni—Ti alloy with an outer diameter of 0.495 mm was used as a core wire.

Example 4

An aspiration catheter was produced as in Example 3 except that a straight wire composed of SUS304 alloy steel with an outer diameter of 0.385 mm was used as a core wire.

Example 5

An aspiration catheter was produced as in Example 3 except that a straight wire composed of an Ni—Ti alloy with an outer diameter of 0.880 mm was used as a core wire.

Example 6

An aspiration catheter was produced as in Example 1 except that a tapered wire composed of SUS304 alloy steel with an outer diameter at the proximal end of 0.605 mm, an outer diameter at the distal end of 0.385 mm, and a length of the tapered portion of 600 mm was used as a core wire.

Example 7

An aspiration catheter was produced as in Example 1 except that a spring wire composed of SUS304 alloy steel with an outer diameter of 0.605 mm (0.150 mm wire closely coiled around 0.300 mm core wire) was used as a core wire.

Example 8

An aspiration catheter was produced as in Example 1 except that a braided tube with an outer diameter of 1.30 mm, an inner diameter of 1.10 mm, and a length of 1,100 mm was used as a proximal shaft, the braided tube including a metal braid formed using metal wires composed of SUS304 alloy steel with a size of 0.10 mm×0.03 mm (one metal wire per group, 16 groups), an inner layer composed of polytetrafluoroethylene (POLYFLON F-207, Daikin Industries, Ltd.), and an outer layer composed of a polyamide elastomer (PEBAX7233SA01, Elf Atochem, Inc.); and that a tube with an outer diameter of 0.60 mm, and inner diameter of 0.42 mm, and a length of 10 mm was formed by extrusion molding of a polyamide elastomer (PEBAX7233SA01, Elf Atochem, Inc.), and a radiopaque marker composed of a platinum-tungsten alloy (tungsten content 8 wt %) with an outer diameter of 0.72 mm, an inner diameter of 0.65 mm, and a length of 1 mm was fixed by swaging on the center of the tube to produce a guidewire shaft.

Example 9

An aspiration catheter was produced as in Example 1 except that a straight wire composed of SUS304 alloy steel with an outer diameter of 0.275 mm was used as a core wire.

Example 10

An aspiration catheter was produced as in Example 1 except that a straight wire composed of SUS304 alloy steel with an outer diameter of 1.05 mm was used as a core wire.

Comparative Example 1

An aspiration catheter was produced as in Example 1 except that no core wire was used.

(Evaluation of Kinking Resistance During Insertion and Passability Through Bent Portion)

Figure 8:
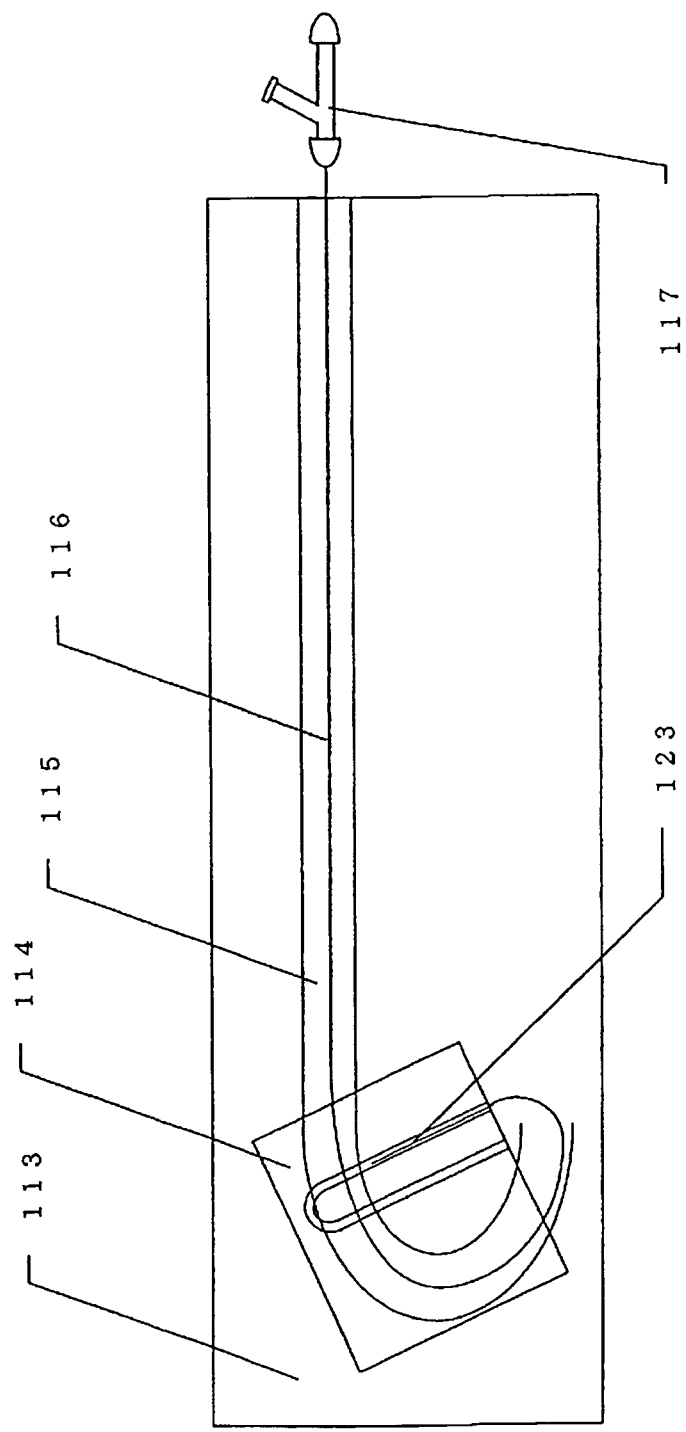
FIG. 8 is a schematic diagram showing a method for evaluating kinking resistance and passability through a bent portion with respect to aspiration catheters of the present invention.
Figure 9:
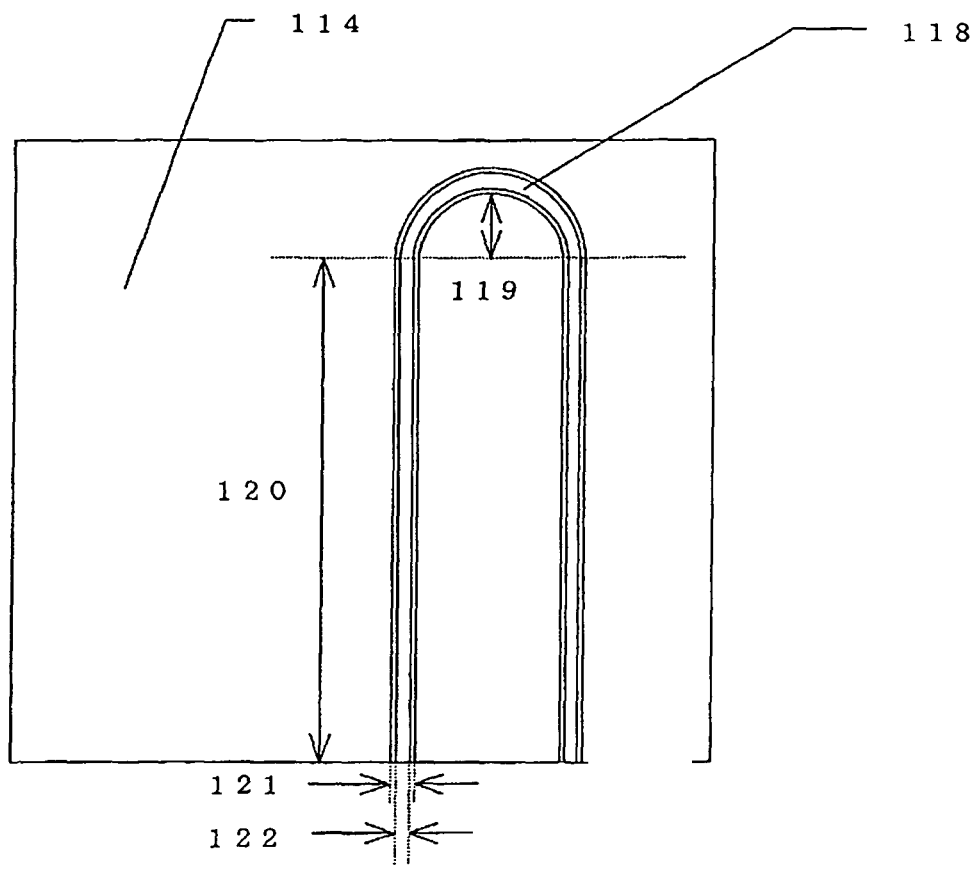
FIG. 9 is an enlarged view of a plate including a bent portion shown in FIG. 8.
Figure 10:
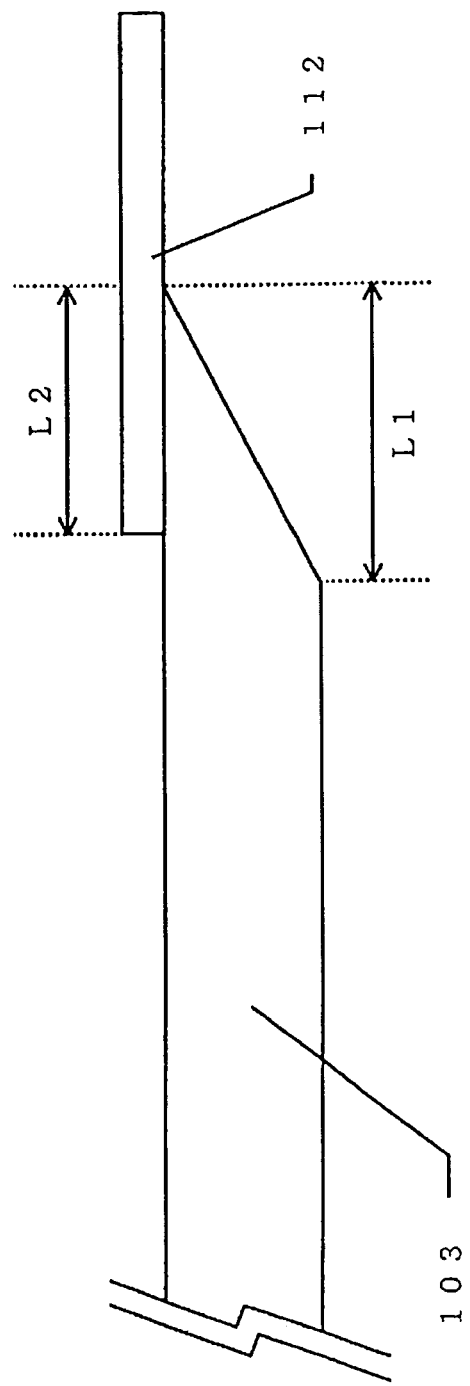
FIG. 10 is an example of L1 and L2.

As shown in FIG. 8, a simulated aorta 115 and a guiding catheter 116 were disposed in a tank 113 filled with a physiological saline solution kept at 37° C., and a hemostasis valve 117 was fixed to the guiding catheter 116. The tip of the guiding catheter 116 was connected to a plate 114 provided with a simulated coronary artery, and a guidewire 123 with an outer diameter of 0.014 inch was preliminarily passed through the guiding catheter. As shown in FIG. 9, a polyethylene tube 118 serving as a simulated coronary artery was disposed in the plate 114, and the polyethylene tube 118 included a bent portion 119 and a linear portion 120. The bent portion 119 had a radius of curvature of 15 mm, and the linear portion 120 had a length of 80 mm. The polyethylene tube 118 had an outer diameter 121 of 5 mm and an inner diameter 122 of 3 mm. Each of the aspiration catheters in the examples and comparative examples was inserted into the guiding catheter 116 over the guidewire 123 from the hemostasis valve 117, and occurrence of kinking and passability through the bent portion 119 were evaluated. The results are shown in Table 1.

In Table 1, evaluation criteria were as follows:
Kinking Resistance
○: Excellent
Δ: Fair
x: Poor
Passability
○: Excellent
Δ: Fair
x: Poor

TABLE 1

| | Material for proximal shaft | Shape of core wire | Material for core wire | R1 [mm] | R1/R2 | Kinking resistance | Passability |
|---|---|---|---|---|---|---|---|
| Example 1 | Polyimide | Straight | SUS304 | 0.605 | 0.55 | ○ | ○ |
| Example 2 | Polyimide | Straight | SUS304 | 0.715 | 0.65 | ○ | ○ |
| Example 3 | Polyimide | Straight | Ni—Ti alloy | 0.495 | 0.45 | ○ | ○ |
| Example 4 | Polyimide | Straight | SUS304 | 0.385 | 0.35 | Δ | ○ |
| Example 5 | Polyimide | Straight | Ni—Ti alloy | 0.880 | 0.80 | ○ | Δ |
| Example 6 | Polyimide | Tapered | SUS304 | 0.605 | 0.55 | ○ | ○ |
| Example 7 | Polyimide | Spring wire | SUS304 | 0.605 | 0.55 | ○ | ○ |
| Example 8 | Braided tube | Straight | SUS304 | 0.605 | 0.55 | ○ | ○ |
| Example 9 | Polyimide | Straight | SUS304 | 0.275 | 0.25 | Δ | ○ |
| Example 10 | Polyimide | Straight | SUS304 | 1.05 | 0.95 | ○ | Δ |
| Comparative Example 1 | Polyimide | — | — | — | — | x | Δ |

In each of Examples 1 to 8 according to the present invention, kinking did not substantially occur in the aspiration catheter, and relatively good passability through the bent portion was shown.

In each of Examples 1 to 3 and 6 to 8, no kinking occurred in the aspiration catheter, and also passability through the bent portion was excellent.

On the other hand, in Comparative Example 1, the aspiration catheter did not show sufficient performance.

INDUSTRIAL APPLICABILITY

As described above, in accordance with the present invention, it is possible to easily provide an aspiration catheter for removing by aspiration a substance from a living body, the catheter including an aspiration lumen for removing by aspiration a substance, the aspiration lumen extending to a hub provided at the proximal end of the catheter; and a detachable core wire disposed in the aspiration lumen. The aspiration catheter is sufficiently flexible to satisfactorily track tortuous blood vessels, and the possibility of kinking of the catheter shaft is decreased when the aspiration catheter is inserted into a guiding catheter from outside of the body, and thus good operationality is achieved.

The invention claimed is:

1. An aspiration catheter configured for insertion into a living body and for aspirating a thrombi from the living body, comprising:
   a main shaft including a distal shaft and a proximal shaft, wherein an aspiration lumen removes the thrombi by aspiration is disposed in the main shaft;
   a guidewire shaft disposed at a distal region of the distal shaft, the guidewire shaft having a guidewire lumen into which a guidewire is insertable, the guidewire lumen being disposed in the guidewire shaft;
   a hub provided at a proximal end of the proximal shaft, the aspiration lumen extending to the hub; and
   a core wire disposed in the aspiration lumen, a proximal end of the core wire extending out of the aspiration lumen and being mounted to a proximal end of the hub via a connector attached to the core wire, and the core wire being removable during the removal by aspiration of the thrombi from the living body, wherein
   a relationship 0.4≤a maximum outer diameter of the core wire/a minimum inner diameter of the aspiration lumen≤0.7 is satisfied,
   the aspiration lumen extends to an opening at a distal end of the distal shaft, and
   the distal end of the core wire is located away from the distal end of the aspiration lumen in the proximal direction when the core wire is disposed in the aspiration lumen.

2. The aspiration catheter according to claim 1, wherein a connector is fixed on the proximal end of the core wire, and the connector is mounted to the proximal end of the hub in a detachable manner.

3. The aspiration catheter according to claim 2, wherein the interior of the aspiration lumen can be flushed through the connector with the connector being mounted to the proximal end of the hub in a detachable manner.

4. The aspiration catheter according to claim 1, wherein the core wire is a spring wire comprising a coiled metal wire.

5. The aspiration catheter according to claim 1, wherein at least a portion of the core wire has a tapered shape in which the outer diameter becomes larger toward the proximal end of the core wire.

6. The aspiration catheter according to claim 1, wherein at least a portion of the core wire has flexibility which becomes higher toward the distal end of the core wire.

7. The aspiration catheter according to claim 1, wherein the core wire comprises stainless steel, a Co—Cr alloy, an Ni—Ti alloy, an Ni—Ti—Fe alloy, an Ni—Ti—Cu alloy, an Ni—Ti—Cr alloy, an Ni—Ti—V alloy, an Ni—Ti—Co alloy, an Ni—Ti—Nb alloy, an Ni—Ti—Pd alloy, an Ni—Ti—Cu—Cr alloy, or a composite thereof.

8. The aspiration catheter according to claim 1, wherein the tip of the distal shaft is obliquely cut, the distal end of the guidewire shaft is positioned at the obliquely cut distal end of the distal shaft or protrudes from the distal end of the distal shaft in the distal direction, and the relationship 0.5≤L2/L1 is satisfied, wherein L1 is the length of the obliquely cut portion of the distal shaft in the longitudinal direction of the catheter, and L2 is the length from the proximal end of the guidewire shaft to the distal end of the distal shaft.

9. The aspiration catheter according to claim 8, wherein the relationship 2 mm≤L1≤10 mm is satisfied.

10. The aspiration catheter according to claim 1, wherein the guidewire shaft is provided with a radiopaque marker.

11. The aspiration catheter according to claim 1, wherein the proximal shaft comprises a polyimide.

12. The aspiration catheter according to claim 1, wherein the proximal shaft comprises a braided tube in which a metal braid and a polymer material are combined.

13. The aspiration catheter according to claim 12, wherein the braided tube comprises an inner layer defining the aspiration lumen, a metal braid disposed on the outer surface of the inner layer, and an outer layer disposed on the outer surface of the metal braid.

14. The aspiration catheter according to claim 1, wherein at least a proximal portion of the proximal shaft has a flexural modulus of 1 GPa or more.

15. The aspiration catheter according to claim 1, wherein at least a portion of the distal shaft is applied with a hydrophilic coating that exhibits a lubricating property in a wet environment.

16. A method for using the aspiration catheter according to claim 1, the method comprising the steps of inserting the aspiration catheter into a living body with the core wire being present in the aspiration lumen, then withdrawing the core wire, and applying a negative pressure to the aspiration lumen to remove by aspiration a thrombi from the living body.

17. The aspiration catheter according to claim 1, wherein the core wire has a straight shape.

* * * * *